(12) United States Patent
Chen

(10) Patent No.: US 8,865,888 B2
(45) Date of Patent: Oct. 21, 2014

(54) COMPOSITE GLUCAN AND METHOD FOR PREPARING THE SAME

(75) Inventor: Shiu-Nan Chen, Taipei (TW)

(73) Assignees: Shiu-Nan Chen, Taipei (TW); Sher-Win Chen, San Marino, CA (US); Jung-Fu Wu, San Marino, CA (US)

( * ) Notice: Subject to any disclaimer, the term of this patent is extended or adjusted under 35 U.S.C. 154(b) by 97 days.

(21) Appl. No.: 13/560,959

(22) Filed: Jul. 27, 2012

(65) Prior Publication Data

US 2014/0031542 A1 Jan. 30, 2014

(51) Int. Cl.
*C12P 19/04* (2006.01)
*C08B 37/00* (2006.01)

(52) U.S. Cl.
CPC .............. *C08B 37/0003* (2013.01); *C12P 19/04* (2013.01)
USPC ...................................... 536/123.12; 435/101

(58) Field of Classification Search
CPC .............................. C08B 37/0003; C12P 19/04
USPC ....................................... 536/123.12; 435/101
See application file for complete search history.

(56) References Cited

U.S. PATENT DOCUMENTS

| | | | |
|---|---|---|---|
| 2003/0021829 | A1 | 1/2003 | Hamano et al. |
| 2004/0266725 | A1 | 12/2004 | Inohara et al. |

FOREIGN PATENT DOCUMENTS

| | | | |
|---|---|---|---|
| CN | 101768541 | * | 7/2010 |
| JP | 11080206 | * | 3/1999 |
| JP | 2001-247466 A | | 10/2002 |
| JP | 2003-128588 A | | 5/2003 |

OTHER PUBLICATIONS

Papaspyridi et al. Optimization of biomass production with enhanced glucan and dietary fibres content by *Pleurotus ostreatus* ATHUM 4438 under submerged culture. Biochem Engineering J 50:131-138, 2010.*
New insights on trehalose a multifunctional molecule; Glycobiology, vol. 12, No. 4, pp. 17R-27R, 2003.
Preservation of mammalian cells learning nature's tricks; Nature Biotechnology; vol. 18, pp. 145-146; Feb. 2000.
Trehalose a review of properties, history of use and human tolerance, and results of multiple safety studies; Food and Chemical Toxicology 40 (2002) 871-898.
Trehaloses; Advances in Carbohydrate Technology; pp. 201-225; Jul. 27, 2000.
The role of trehalose and other carbohydrates in biopreservation; Biotechnology and Genetic engineering Reviews; vol. 11, (1993) pp. 263.
Production of trehalose by adual enzyme system of immobilized maltose phosphorylase and trehalose phosphorylase; Enzyme and Microbial Technology 22:71-75, 1998.
Novel functions and applications of trehalose; Pure Appl. Chem., vol. 74, No. 7, pp. 1263-1269, 2002.
A Highly Efficient Method for Long-Chain cDNA Synthesis Using Trehalose and Betaine; Analytical Biochemistry 301, 168-174(2002).
Intracellular trehalose improves the survival of cryopreserved mammalian cells; Nature Biotechnology vol. 18 Feb. 2000; pp. 163.
Trehalose production: exploiting novel approaches; Trends in Biotechnology vol. 20 No. 10 Oct. 2002; pp. 420-425.
Trehalose Eye Drops in the Treatment of Dry Eye Syndrome; Ophthalmology 2002;109:2024-2029.

* cited by examiner

*Primary Examiner* — Brandon Fetterolf
*Assistant Examiner* — Yih-Horng Shiao
(74) *Attorney, Agent, or Firm* — Venable, Campillo, Logan & Meaney, P.C.

(57) ABSTRACT

A composite glucan is disclosed. The composite glucan of the present invention includes a mushroom glucan synthesized from a culture medium containing trehalose and mannose. The composite glucan of the present invention has great moisture retention and can be used in eye drops for alleviating xerophthalmia. A method for preparing a composite glucan is also disclosed.

9 Claims, 2 Drawing Sheets

COMPOSITE GLUCAN AND METHOD FOR PREPARING THE SAME

FIELD OF INVENTION

The present invention relates to a glucan and a method for preparing the glucan, and more particularly, to a composite glucan synthesized from a culture medium having trehalose and mannose.

BACKGROUND OF THE INVENTION

Trehalose is a non-reducing disaccharide formed by an α,α-1,1-glucoside bond formed by an α,α-1,1-glucoside bond (Elbein et al., 2003), having a formula of $C_{12}H_{22}O_{11}$ and named as α-D-glucopyranosyl α-D-glucopyranoside. Trehalose can be found in bacteria, yeast, fungi, algae, plants and invertebrates. Trehalose can contact cell membranes to maintain fluidity and thus prevent the change of membrane fusion and membrane permeability (Crowe & Crowe, 2000; Richards et al., 2002). Trehalose is not easy to be hydrolyzed by α-glucosidase, has great stability in solution, and has the solubility and osmolality similar to maltose. At 92% humidity, trehalose has 9.54% of water, and has chemical stability (Birch et al., 1963; Richards et al., 2002).

In organisms, trehalose can store energy, and protect proteins and cell membranes under heat, frozen, dry or high osmotic pressure (Newman et al., 1993). In many kinds of bacteria, trehalose can stabilize functions of cell walls (Richards et al., 2002). Trehalose can store energy in plants and animals, facilitate plants to grow in dry environments, and help yeasts to get used to changes of environment such as dryness, changes of osmotic pressure, heat shock and tolerance to alcohol (Yoshida et al., 1998). Trehalose can be used in food, medicines (Higashiyama, 2002) and biotechnology (Spriess and Ivell, 2002). A proper amount of trehalose can be used for increasing cell viability (Eroglu et al., 2000). Trehalose is proved as a GRAS (generally regarded as safe) food by FDA, and is widely used in food, cosmetics and medical products. Trehalose is used as a stabilizing agent for enzymes, proteins, biomass preparation of pharmaceutical compositions and organ transplants, used as an anti-freezing agent for vaccines and mammalian cells, and used as a moisturizing agent with liposomes (Schiraldi et al., 2002). Further, trehalose may be formed in organisms via genetic recombination.

Mannose plays critical roles in various cellular activities. Mannose is critical in activating macrophages and thus activates anti-inflammation and tissue regeneration. Macrophages have four different receptors for mannose to clean residual bodies resulting from inflammation. Mannose has anti-inflammation ability for activating fibroblasts to produce collagen and proteoglycans at healing of wounds. Mannose is considered to be natural anti-inflammation material to modulate over-activated neutrophils. All cells contain mannose, and thus mannose can affect all organs and tissues in a body. It is found that there is mannose on the photoreceptor in the retina, and plays a critical role in vision. The supplement of mannose can be combined with other treatments for diabetes patients with cataract. Mannose can maintain the metabolism of cell membranes and thus can protect eye lens.

Xerophthalmia is a medical condition in which the eye fails to produce tears due to the dryness of epithermal cells of cornea. Currently, there are various compositions such as artificial tears for treating xerophthalmia. Trehalose has great moisture retention property, and has been used in eye drops for treating xerophthalmia (Matsuo et al., 2002). JP 2003-128588 issued on May 8, 2003 discloses that the polysaccharide composition is used as a matrix in eye drops, wherein the agar can be used as a matrix of eye drops for enhancing the medicine to move into eyes. JP 2001-247466 issued on Sep. 11, 2011 discloses that an eye drop for contact lens to absorb polyvinylpyrrolidone so as to stabilize the tear film. The conventional eye drop includes polysaccharides but lacks long term moisture retention. Furthermore, small molecular weight polysaccharides in the conventional eye drop fail to activate the immune system.

Accordingly, there is a need to develop a new material for eye drops.

SUMMARY OF THE INVENTION

The present invention provides a composite glucan, including a mushroom glucan synthesized from a culture medium having trehalose and mannose.

In accordance with the present invention, the mushroom glucan has a molecular weight in a range from 35000 to 2000000 Da.

In an embodiment of the present invention, the composite glucan includes at least two kinds of mushroom glucans. For example, the mushroom which the at least two kinds of mushroom glucans belong to is at least one selected from the group consisting of *Ganoderma lucidum, Antrodia comphorata, Agaricus brazil, Coriolus versicolor* and *Schizophyllum commune*.

The present invention further provides a method for preparing a composite glucan. The method of the present invention includes the steps of preparing a culture medium containing trehalose and mannose; preparing a culture of mushroom mycelium in the culture medium; homogenizing the culture medium having the culture of mushroom mycelium to form a homogeneous solution; filtering the homogeneous solution to obtain a glucan solution; and performing a precipitation to precipitate a mushroom glucan.

In accordance with the method of the present invention, the culture medium further includes a yeast extract.

According to an embodiment of the present invention, the culture medium includes 5 wt % of trehalose, 5 wt % of mannose and 1 wt % of the yeast extract. At least two kinds of mushroom mycelia are independently cultured in the culture medium to form at least two culture media. For example, the mushroom which the at least two kinds of mushroom glucans belong to is at least one selected from the group consisting of *Ganoderma lucidum, Antrodia comphorata, Agaricus brazil, Coriolus versicolor* and *Schizophyllum commune*.

Different mushrooms are cultured for various durations. For example, the *Ganoderma lucidum* is cultured for 13 to 15 days, the *Agaricus brazil* is cultured for 20 to 22 days, the *Agaricus brazil* is cultured for 13 to 15 days, the *Coriolus versicolor* is cultured for 20 to 22 days, and the *Schizophyllum commune* is cultured for 4 to 6 days.

In accordance with an embodiment of the present invention, one of the at least two culture media is mixed with the same volume of the other of the at least two culture media for homogenization.

In an embodiment of the present invention, the homogeneous solution is filtered via a ceramic filtration membrane to remove molecules having a molecular weight less than 30000 Da.

Moreover, the present invention provides an eye drop, which includes a mushroom glucan synthesized from a culture medium containing trehalose and mannose.

The present invention provides a composite glucan, which includes a mushroom glucan synthesized from a culture medium having trehalose and mannose. The composite glucan of the present invention has great moisture retention capability, and has β-glucan and active peptides for activating macrophages in eyes, eliminating residual bodies and protein precipitates due to autoimmune so as to enhance cell regeneration, and reducing cell aging in eyes via anti-oxidation. The composite glucan of the present invention has significant efficacy, which small molecular weight polysaccharides or the combination thereof cannot achieve.

DETAILED DESCRIPTION OF THE PREFERRED EMBODIMENTS

The following specific examples are used for illustrating the present invention. A person skilled in the art can easily conceive the other advantages and effects of the present invention.

The present invention provides a composite glucan, which can be used safely and stably in eyes.

Further, the present invention provides a method for preparing a composite glucan. In the method of the present invention, a culture medium including trehalose and mannose is prepared. In an embodiment of the present invention, the culture medium includes a yeast extract. The culture medium includes 5 wt % of trehalose, 5 wt % of mannose and 1 wt % of the yeast extract, and is autoclaved at a high pressure and a high temperature for three minutes (121° C., 1.5 Ib).

The culture medium is cooled down at the room temperature, and then at least two kinds of mushroom mycelia are independently cultured in the culture medium. The mushroom which the at least two kinds of mushroom mycelia belong to is at least one selected from the group consisting of *Ganoderma lucidum*, *Antrodia comphorata*, *Agaricus brazil*, *Coriolus versicolor* and *Schizophyllum commune*.

Different mushrooms are cultured for various durations. For example, the *Ganoderma lucidum* is cultured for 13 to 15 days, the *Agaricus brazil* is cultured for 20 to 22 days, the *Agaricus brazil* is cultured for 13 to 15 days, the *Coriolus versicolor* is cultured for 20 to 22 days, and the *Schizophyllum commune* is cultured for 4 to 6 days. During the culture, the mycelia are respectively cultured under shaking, and thus each mycelium produces a large amount of glucans in the culture medium. Then, all culture media are mixed at the same volume. The mixture is homogenized by a homogenizer (Polytron PT6000, Switzerland) at 30,000 rpm for 3 minutes to form a homogeneous solution.

Then, the homogeneous solution is filtered, and thus a glucan solution is obtained. In an embodiment of the present invention, the homogeneous solution is filtered by a filter (200 mesh/mm$^2$), then filtered via a ceramic filtration membrane (50 kD (0.3 μm) pore size, TAMI Industries, France) to remove molecules having a molecular weight less than 30000 Da, and thus the glucan solution is obtained.

The precipitation is performed to precipitate a mushroom glucan. For example, the glucan solution is provided in ethanol (1:4 v/v), and the mixture is placed at the room temperature for 2 to 3 hours. Upon precipitation, the crystal precipitates are obtained. The precipitates are dried by a drier (CHRIST LOC-1). The dried powders are dissolved in water, and the solution is mixed under shaking, such that the composite glucan is formed for eye drops.

HPLC Analysis of Eye Drops

The composite glucan of the present invention was used for preparing the eye drops shown in Table 1. The eye drops were analyzed by HPLC.

Pretreatment of samples: 1 ml of the eye drop was filtered via the 0.45 μm membrane for the subsequent analysis.

Figure 1:
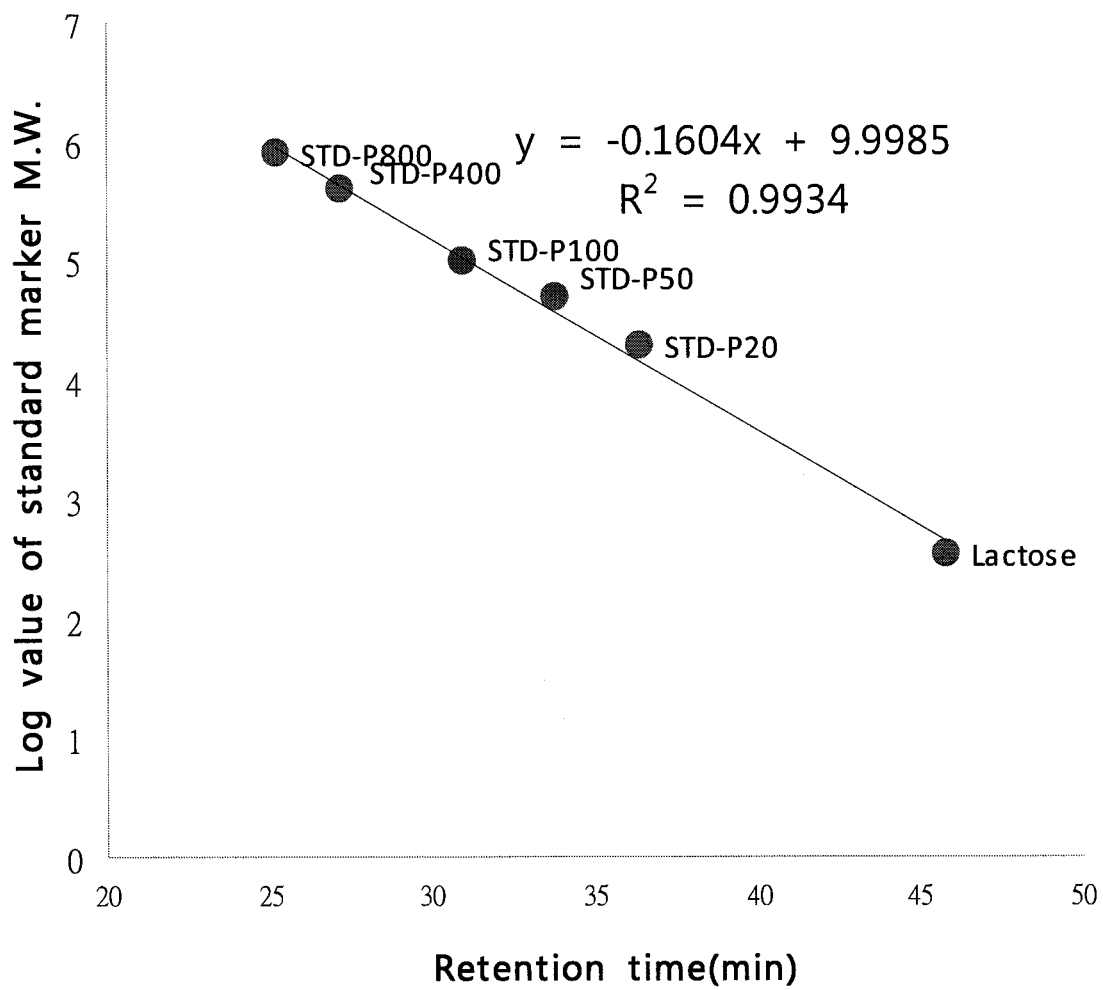
FIG. 1 is a diagram showing the test result in the HPLC analysis according to the present invention.

The conditions for the HPLC analysis were shown in Table 2 and Table 3. The analysis results were shown in FIG. 1 and FIG. 2.

TABLE 1

Composition of eye drops

| Composition | Content (%) (weight/volume) |
|---|---|
| Cyanocobalamin | 0.00005 |
| Chlorobutanol | 1.5 |
| Boric acid | 10 |
| Composite glucan | 15 |
| EDTA disodium | 0.2 |
| Sodium borate | 2 |
| Water | a proper amount |

TABLE 2

Conditions for analysis: RI2000 detector

| Date | Dec. 26, 2010 | Temperature | Room temperature 23-25° C. |
|---|---|---|---|
| Column | KS-G | Mobile phase | ddH$_2$O |
| | KS-804 | Flow rate | 0.5 ml/min |
| | KS-805 | Injection volume | 20 μl |
| | | Total pressure | 450 psi |

TABLE 3

Samples

| Name | Molecular weight (M.W.) |
|---|---|
| STD-P800 | 800,000 |
| STD-P400 | 400,000 |
| STD-P100 | 100,000 |
| STD-P50 | 50,000 |
| STD-P20 | 20,000 |
| Lactose | 360 |

Figure 2:
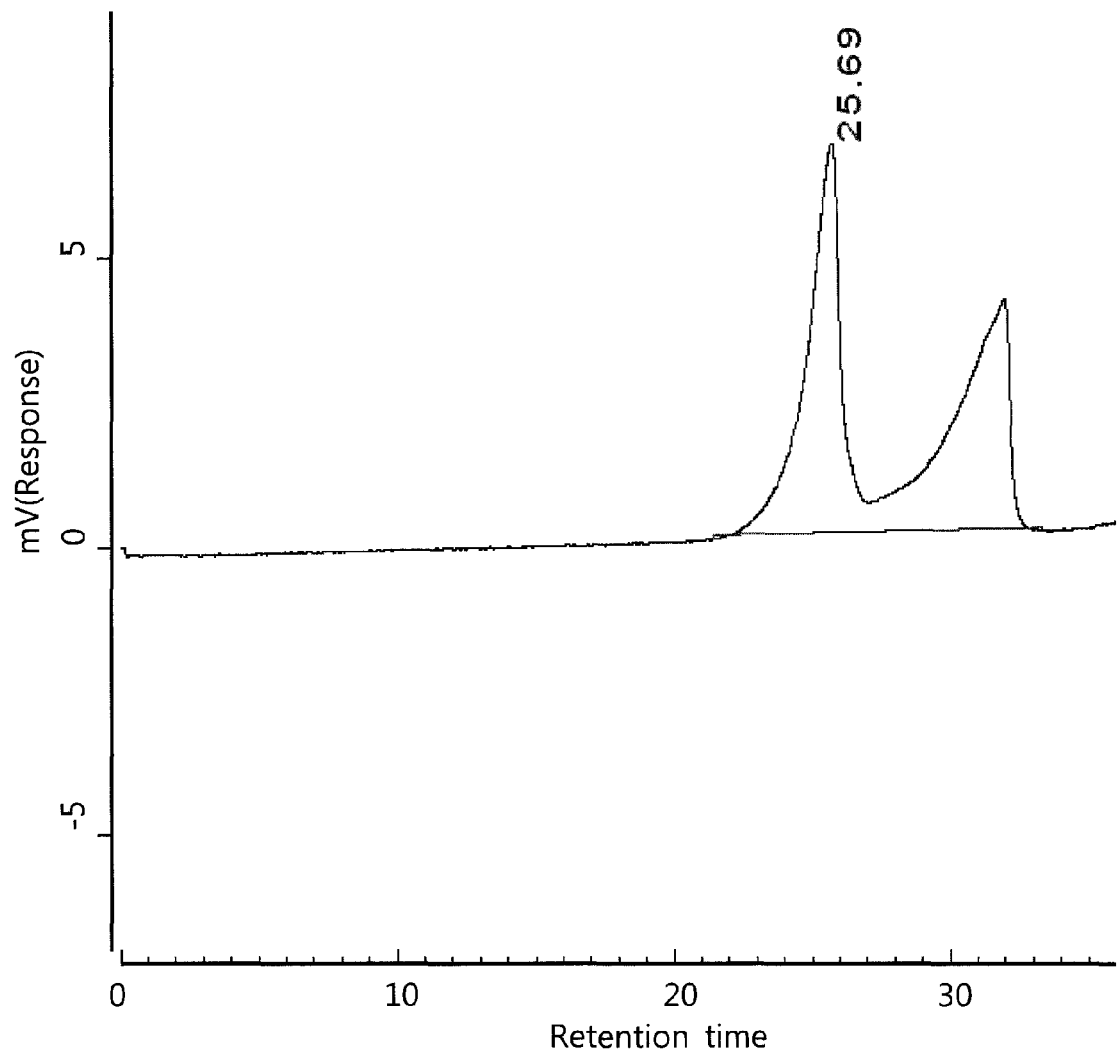
FIG. 2 is a diagram showing the test result of the eye drops in the HPLC analysis according to the present invention.

As shown in FIG. 2, the retention time of the composite glucan of the present invention is 25.69 min. Upon calculation, the molecular weight of the glucan of the present invention is 38637 to 2558857 Da. It is shown that the samples have a lot of the composite glucan of the present invention, and the composite of the present invention has high stability.

The invention has been described using exemplary preferred embodiments. However, it is to be understood that the scope of the invention is not limited to the disclosed arrangements. The scope of the claims, therefore, should be accorded the broadest interpretation, so as to encompass all such modifications and similar arrangements.

What is claimed is:

1. A method for preparing a composite mushroom glucan, comprising the steps of:
    preparing a culture medium containing trehalose and mannose;
    preparing a culture of a mushroom mycelium in the culture medium;
    homogenizing the culture medium having the culture of the mushroom mycelium to form a homogeneous solution;

filtering the homogeneous solution to obtain a glucan solution; and performing a precipitation to precipitate a mushroom glucan, wherein at least two kinds of the mushroom mycelium are independently cultured in the culture medium to form at least two cultures, and one of the at least two cultures is mixed with the same volume of the other of the at least two cultures for homogenization.

2. The method of claim 1, wherein the culture medium includes a yeast extract.

3. The method of claim 2, wherein the culture medium includes 5 wt % of trehalose, 5 wt % of mannose and 1 wt % of the yeast extract.

4. The method of claim 1, wherein the mushroom mycelium belongs to at least a mushroom selected from the group consisting of *Ganoderma lucidum, Antrodia comphorata, Agaricus brazil, Coriolus versicolor* and *Schizophyllum commune*.

5. The method of claim 4, wherein the *Ganoderma lucidum* is cultured for 13 to 15 days, the *Antrodia comphorata* is cultured for 20 to 22 days, the *Agaricus brazil* is cultured for 13 to 15 days, the *Coriolus versicolor* is cultured for 20 to 22 days, and the *Schizophyllum commune* is cultured for 4 to 6 days.

6. The method of claim 1, wherein the homogeneous solution is filtered via a ceramic filtration membrane to remove molecules having a molecular weight less than 30000 Da.

7. The method of claim 1, wherein the precipitation is performed by using ethanol.

8. The method of claim 1, wherein the mushroom glucan has a molecular weight in a range from 35000 to 2000000 Da.

9. The method of claim 1, wherein the mushroom glucan has a molecular weight in a range from 38673 to 2448857 Da.

* * * * *